United States Patent
Jarrell et al.

(10) Patent No.: US 7,863,561 B2
(45) Date of Patent: Jan. 4, 2011

(54) MASS-SPECTROMETER INTERFACE HOUSING

(75) Inventors: Joseph A. Jarrell, Newton Highlands, MA (US); Stanislaw Koziol, Wrentham, MA (US); Peter Pino, North Attleboro, MA (US); Theodore D. Ciolkosz, Milton, MA (US)

(73) Assignee: Waters Technologies Corporation, Milford, MA (US)

( * ) Notice: Subject to any disclaimer, the term of this patent is extended or adjusted under 35 U.S.C. 154(b) by 388 days.

(21) Appl. No.: 11/917,771

(22) PCT Filed: Jun. 26, 2006

(86) PCT No.: PCT/US2006/024695
§ 371 (c)(1),
(2), (4) Date: Jun. 25, 2008

(87) PCT Pub. No.: WO2007/002537
PCT Pub. Date: Jan. 4, 2007

(65) Prior Publication Data
US 2009/0218487 A1 Sep. 3, 2009

Related U.S. Application Data

(60) Provisional application No. 60/693,721, filed on Jun. 24, 2005.

(51) Int. Cl.
*H01J 49/00* (2006.01)
(52) U.S. Cl. ............... 250/288; 250/281; 250/282; 250/289
(58) Field of Classification Search .............. 250/281, 250/282, 288, 289
See application file for complete search history.

(56) References Cited

U.S. PATENT DOCUMENTS

| 5,753,910 A | 5/1998 | Gourley et al. |
| 2004/0094706 A1 | 5/2004 | Covey et al. |

*Primary Examiner*—Jack I Berman
*Assistant Examiner*—Hanway Chang
(74) *Attorney, Agent, or Firm*—Jamie H. Rose

(57) ABSTRACT

An apparatus for performing chemical analyses includes a mass spectrometry module and an interface module that processes sample materials for delivery to the mass spectrometry module. The interface module includes a vessel having an opening to access a vessel chamber, a door to block the opening, a sealing member disposed between the door and the vessel, and an interlock. The interlock is actuated by the sealing member if the door is in the closed position and the sealing member is properly disposed between the door and the vessel to seal the vessel. The sealing member alternatively includes an indicator portion that is visible to an operator if the door is in the closed position and the sealing member is properly disposed.

20 Claims, 3 Drawing Sheets

MASS-SPECTROMETER INTERFACE HOUSING

FIELD OF THE INVENTION

The present invention relates to mass spectrometers, and, more particularly, to sample-introduction interfaces for mass spectrometers.

BACKGROUND OF THE INVENTION

In some chemical-analysis instruments, the coupling of a liquid chromatograph (LC) to a mass spectrometer (MS) involves an interface that processes the output of the LC to provide suitably ionized sample components for mass analysis by the MS. For example, some interfaces nebulize a fluidic eluent emerging from the LC.

An electrospray interface (ESI), for example, typically directs a chromatographic eluent, including analyte and solvent, through a conductive capillary tube. A charge is transferred from the tube to an aerosol of analyte and solvent that sprays from an exit orifice of the tube. Typically, a neutral carrier gas is mixed with the aerosol to promote evaporation of the solvent and formation of separated ionized analyte molecules suited to mass spectrometric analysis.

ESI and other techniques primarily involve electrostatic nebulization with, or without, pneumatic, thermal, or ultrasonic assistance to form droplets of a liquid stream containing an analyte. The droplets may be generated in a heated or unheated gas stream. The gas serves to desolvate the droplets. The droplets shrink as they desolvate, resulting in the formation of atmospheric ions of the analyte. A portion of these ions are then mass analyzed.

Components of an interface are typically enclosed in a vessel, such as a housing or enclosure, that protects the components and confines chemical vapors. Vapors may include common chromatographic solvents that are mildly hazardous. The vessel typically has a door to provide operator access to components in the vessel for adjustment, maintenance, or repair. Reliable operation of the housing is desirable to avoid exposure of operators to hazardous or irritating vapors.

SUMMARY OF THE INVENTION

Some embodiments of the invention arise from the realization that a sealing member of a vessel can be configured to prevent operation of an instrument if the sealing member is not properly positioned to seal the vessel. For example, a gasket or O-ring can be disposed to actuate a switch in an interface housing and/or to be at least partially visible when a door of the housing is in a closed position. Visibility can be provided by cutout(s) and/or window(s) in a door and/or by extended portion(s) of the sealing member. A switch actuated by a gasket or O-ring can act as a safety interlock that prevents operation of the interface if the gasket or O-ring is out of position such that the switch is not actuated when the door is shut.

Accordingly, one embodiment of the invention features an apparatus for performing chemical analyses. The apparatus includes a mass spectrometry module and an interface module. The interface module receives and processes sample material for admission to the mass spectrometry module.

The interface module includes a vessel having an opening to access components disposed inside the vessel, a door to block the opening if the door is in a closed position and provide access to the chamber if the door is in an opened position, a sealing member disposed between the door and the vessel, and an interlock unit. The sealing member seals the vessel if the door is in the closed position and the sealing member is effectively disposed between the door and the vessel. The interlock unit is actuated by the sealing member if the door is in the closed position and the sealing member is properly disposed adjacent to the door. The apparatus optionally includes a chromatography module that delivers a fluid to the interface module.

Another embodiment of the invention features a an apparatus for performing chemical analyses. The apparatus includes a mass spectrometry module and an interface module. The interface module includes a vessel having an opening to access components disposed inside the vessel, a door to block the opening if the door is in a closed position and provide access to the chamber if the door is in an opened position, and a sealing member disposed between the door and the vessel. The sealing member includes an indicator portion that is visible to an operator if the door is in the closed position and the sealing member is effectively disposed between the door and the vessel.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
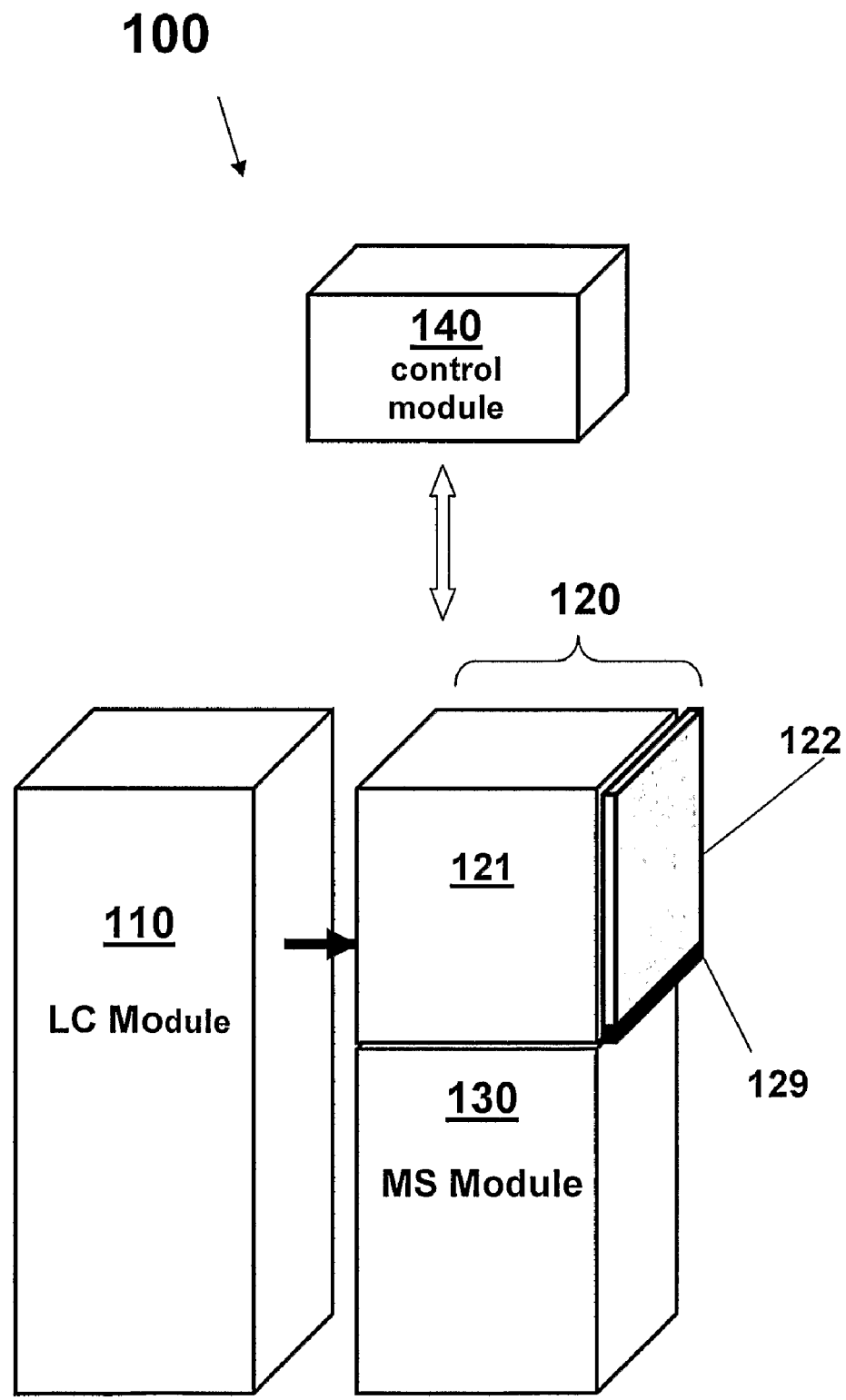
FIG. 1 is a block diagram of an LC/MS instrument, in accordance with one embodiment of the invention.
Figure 2:
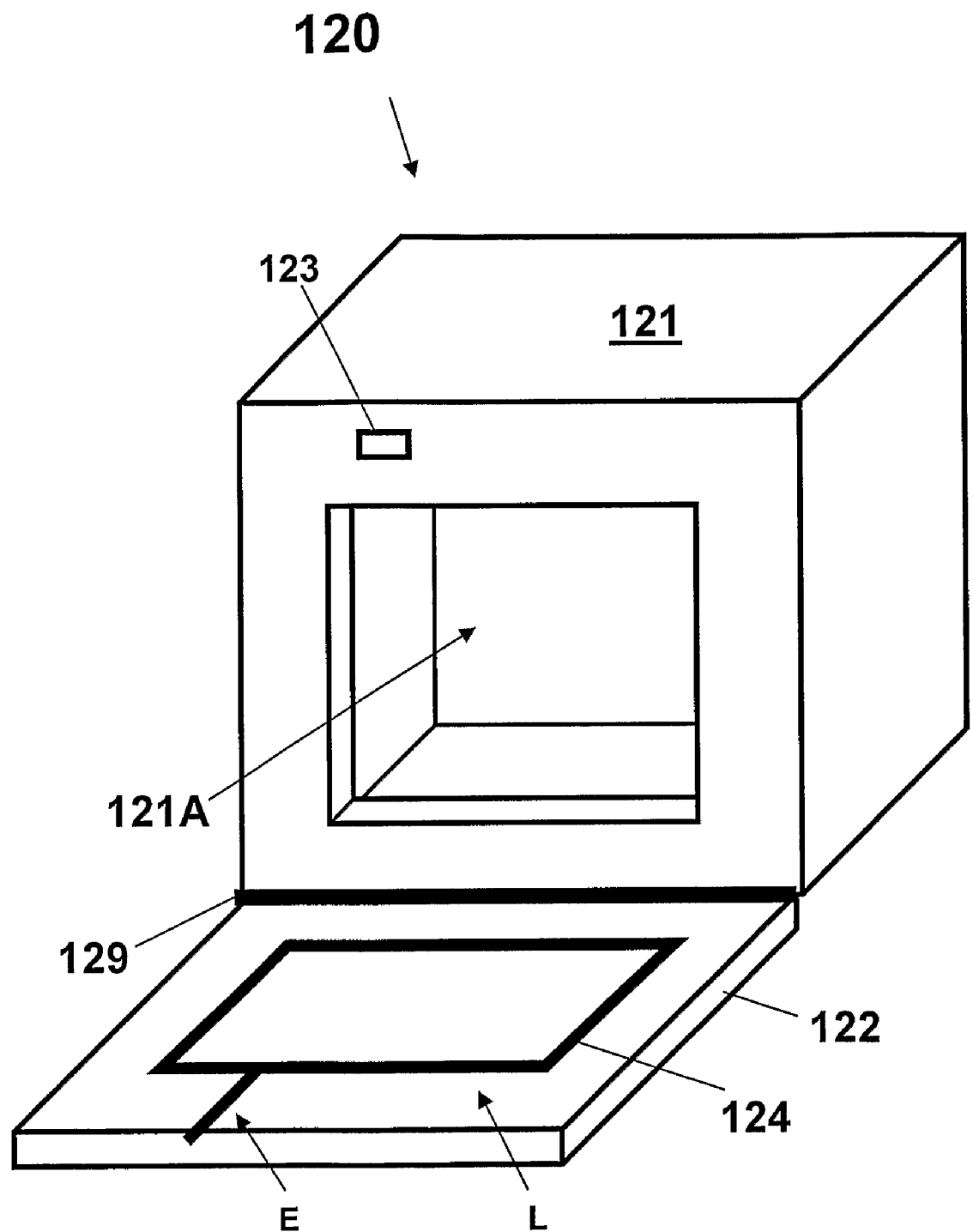
FIG. 2 is a three-dimensional diagram of an interface module of the instrument illustrated in FIG. 1.

FIG. 1 and FIG. 2 illustrate a chemical-analysis instrument 100, in accordance with one embodiment of the invention. FIG. 1 is a block diagram of the instrument 100. The instrument 100 includes a LC module 110, a MS module 130, and an interface module 120 that supports processing of eluent received from the LC module 110 for delivery to the MS module 130.

FIG. 2 is a three-dimensional view of the interface module 120 of the instrument 100, showing the module 120 in greater detail. The interface module 120 includes a vessel 121, an interlock unit 123 attached to the vessel 121, a door 122 for covering an opening in the vessel 121, a hinge component 129 that moveably attaches the door 122 to the vessel 121, and a sealing member 124 to provide a substantially vapor-tight seal between the door 122 and the vessel 121 (the module 120 is shown in an opened state.)

The vessel 121 defines a chamber 121A that houses nebulization-related components for processing of eluent received from the LC module 110. The opening in the vessel 121 provides access to the interior chamber 121A. The vessel 121 optionally has some features, related to configuration and materials, that are similar to that of interface vessels of commercially available LC/MS instruments.

The sealing member 124 is disposed between the door 122 and the vessel 121 during operation of the instrument, and the interlock unit 123 detects the proper presence of the sealing member 124 during operation. The instrument 100 optionally includes a control module 140 that mediates operation of the interface 120 in cooperation with the interlock unit 123.

When the door 122 is closed, the door 122 compresses the sealing member 124 against the vessel 121. The sealing member 124 thus helps to seal the vessel 121 to contain solvent vapors in the chamber 121A before the vapors are exhausted (via, for example, an exhaust port of the vessel 121.)

The interlock 123 mediates operation of the interface module 120 to prevent admission of potentially harmful substances into the chamber 121A if the vessel 121 is not properly sealed. The interlock unit 123 is attached to the vessel 121 adjacent to an edge of the vessel 121 or at any other suitable location.

The interlock unit 123 includes any suitable device to detect the proper presence of the sealing member 124. Suitable devices include an electromechanical switch or other devices known to those having ordinary skill in the electromechanical arts. As described in more detail below, the sealing member 124, when properly positioned between the door 122 and the vessel 121, causes the interlock unit 123 to be actuated when the vessel 121 is closed. Actuation of the interlock unit 123 serves to prove the desired physical state of the vessel 121 for safe operation of the instrument 100.

The sealing member 124 has a cross section like that of a gasket or O-ring or any other suitable configuration. The sealing member 124 includes any suitable material or materials, including known materials, to adequately seal the chamber 121A against escape of vapor. The sealing member 124 is formed of, for example, a suitable compliant material(s), including, for example, known compliant materials such as nitrile, silicone, fluorocarbon, fluorosilicone, ethylene propylene, neoprene, or polyurethane.

In the example embodiment illustrated in FIG. 2, the sealing member 124 has the form of a modified O-ring, having a loop portion L and an extension portion E. The door 122 optionally defines a groove within which the sealing member 124 resides. In some alternative embodiments, the vessel 121 and or the door 122 define grooves within which the sealing member 124 resides. A groove may include, for example, a loop portion and an extension portion to guide placement of a sealing member.

When the sealing member 124 is seated in the groove and/or properly aligned relative to the door 122 and/or vessel 121, the extension E of the sealing member 124 contacts the interlock 123 when the door 122 is in a closed position. Thus, the interface module 120 cannot be operated if the door 122 is closed without placing the sealing member 124 in a proper position or if the sealing member 124 is misaligned such that the sealing member 124 does not actuate the interlock 123.

In some alternative embodiments, the sealing member 124 actuates the interlock 123 by means other than direct contact. For example, an additional intermediate component provides physical contact with the interlock 123. Alternatively, non-physical means are utilized by the interlock to sense the proper placement of the sealing member 124. Any suitable sensing means may be employed.

The extension portion E, or other portion, of the sealing member 124 optionally extends beyond the door 122 to provide and/or improve visibility for an operator. Thus an operator may easily determine if, for example, one has neglected to position the sealing member 124 on the door 122 prior to closing the door 122. Accordingly, a user is alerted to a missing sealing member 124 and is protected from exposure to leaking solvent vapor.

Figure 3:
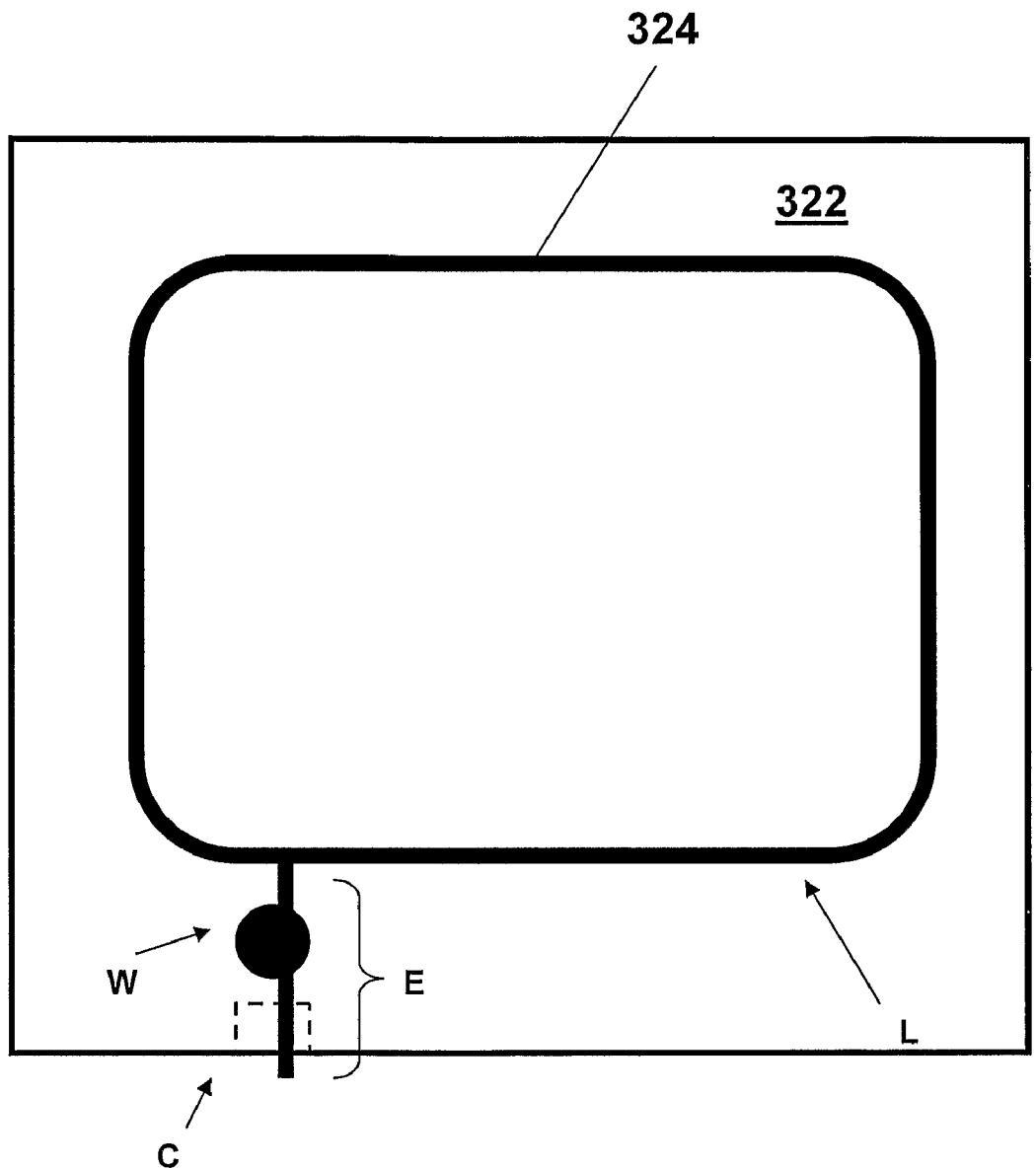
FIG. 3 is a two-dimensional diagram of a door and a sealing member, in accordance with one embodiment of the invention.

FIG. 3 is a two-dimensional diagram of an illustrative embodiment of an alternative door 322 and sealing member 324 combination, which may be used with the instrument 100 illustrated in FIG. 1. The door 322 defines one or more cutout portions C (one shown with dashed lines) located at or away from an edge of the door and through which the sealing member 322 is viewed if the door 322 is in the closed position. Thus, some alternative embodiments provide views of a sealing member in any suitable manner.

The extension portion L of the sealing member 324 includes a wider portion W. The wider portion W is optionally situated such that the wider portion provides contact with the interlock 123 if the sealing member 324 is properly disposed on the door 322 when the door 322 is closed. The wider portion W is optionally utilized to assist positioning of the sealing member 324 in a groove defined in a surface of the door 322.

Again referring to FIG. 1, the control module 140 mediates operation of more or more components of the instrument 100. The control module 140 receives data from and/or provides control signals to the one or more components via wired and/or wireless communications. For example, the control module 140 includes a safety control circuit that receives proof of the proper physical state (closed) from the interlock 123 and responsively permits operation of the interface 120 and/or other portions of the instrument 100.

In various alternative embodiments, the control module 140 includes, for example, a personal computer or workstation and/or is implemented in software, firmware, and/or hardware (e.g., such as an application-specific integrated circuit), and includes, if desired, a user interface.

In view of the description provided above, one having ordinary skill will recognize that numerous alternative configurations are suitable for an interface module. Alternatives utilize an interlock and/or or a visible portion of a sealing member to help assure proper positioning of the sealing member during operation of an instrument.

The instrument 100 is optionally implemented by modifying any suitable commercially available instrument. For example, the LC module 110 includes any suitable chromatography instrument(s), including known instruments, such as column-based instruments. Suitable columns include columns known to one having ordinary skill in the chromatographic arts. The column is formed from, for example, metallic or insulating materials. Suitable materials include known materials such as steel, fused silica, or lined materials. The column optionally includes more than one column, disposed in serial and/or parallel configurations. For example, the column may be a capillary column and may include multiple capillary tubes.

The MS module 130 is any suitable mass spectrometer, including commercially available spectrometers. One suitable mass spectrometer, for example, is a Quattro Premier™ mass spectrometer (available from Waters Corporation, Milford, Mass.)

Variations, modifications, and other implementations of what is described herein will occur to those of ordinary skill without departing from the spirit and the scope of the invention. For example, a door need not be attached via a hinge to a vessel. Moreover, principles of the invention are applicable to numerous devices that utilize O-rings for sealing purposes. Thus, embodiments described herein should not be understood as limiting embodiments of the invention only to applications relating to chromatography and/or mass spectrometry. Accordingly, the invention is to be defined not by the preceding illustrative description but instead by the spirit and scope of the following claims.

What is claimed is:

1. An apparatus for performing chemical analyses, the apparatus comprising:

a mass spectrometry module; and an interface module in communication with an input of the mass spectrometry module to deliver material comprising a sample to the mass spectrometry module, the interface module comprising a vessel defining a chamber and an opening to access components disposed in the chamber, a door to block the opening if the door is in a closed position and provide access to the chamber if the door is in an opened position, a sealing member for disposal substantially between the door and the vessel to seal the vessel if the door is in the closed position, and an interlock unit that is actuated by the sealing member if the door is in the closed position and the sealing member is properly disposed adjacent to the door.

2. The apparatus of claim 1, further comprising a chromatography module in fluid communication with the interface module.

3. The apparatus of claim 1, wherein the sealing member comprises an O-ring.

4. The apparatus of claim 3, wherein the sealing member comprises a loop portion and an extension portion that is attached to the loop portion to actuate the interlock if the door is in the closed state.

5. The apparatus of claim 4, wherein the extension portion comprises a portion having a greater width than a width of the loop portion.

6. The apparatus of claim 4 wherein the door is configured so that the extension portion is visible to an operator if the door is in the closed position and the sealing member is properly positioned intermediate to the door and the vessel.

7. The apparatus of claim 6, wherein the extension portion is visible through a cutout defined by the door.

8. The apparatus of claim 6, wherein the extension portion is visible through a window of the door.

9. The apparatus of claim 4, wherein the extension portion and the loop portion are integrally formed of a same material.

10. The apparatus of claim 4, wherein the extension portion actuates the interlock by direct contact with the interlock.

11. The apparatus of claim 1, wherein the interlock comprises a switch mounted adjacent to the vessel.

12. The apparatus of claim 1, wherein the interface module further comprises a hinge that attaches the door to the vessel.

13. The apparatus of claim 1, further comprising a control module comprising a safety control circuit that receives proof of a proper physical state from the interlock unit and responsively permits operation of the interface.

14. An apparatus for performing chemical analyses, the apparatus comprising:

a mass spectrometry module; and an interface module in communication with an input of the mass spectrometry module to deliver material comprising a sample to the mass spectrometry module, the interface module comprising a vessel defining a chamber and an opening to access components disposed in the chamber, a door to block the opening if the door is in a closed position and provide access to the chamber if the door is in an opened position, and a sealing member for disposal substantially between the door and the vessel to seal the vessel if the door is in the closed position, the sealing member comprising a indicator that is visible to an operator if the door is in the closed position.

15. The apparatus of claim 14, further comprising a chromatography module in fluid communication with the interface module.

16. The apparatus of claim 14, wherein the indicator comprises an extension portion and the sealing member further comprises a loop portion attached to the extension.

17. The apparatus of claim 16, wherein the door is configured so that the extension portion is visible to an operator if the door is in the closed position and the loop portion is properly positioned between the door and the vessel.

18. The apparatus of claim 16, wherein the extension portion and the loop portion are integrally formed of a same material.

19. The apparatus of claim 16, wherein the extension portion is visible through a cutout defined by the door.

20. The apparatus of claim 14, wherein the interface module further comprises a hinge that attaches the door to the vessel.

* * * * *